United States Patent
Predick

(10) Patent No.: US 9,131,963 B2
(45) Date of Patent: Sep. 15, 2015

(54) POSTERIOR CROSS CONNECTOR ASSEMBLY

(75) Inventor: Daniel Predick, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 862 days.

(21) Appl. No.: 13/414,076

(22) Filed: Mar. 7, 2012

(65) Prior Publication Data

US 2012/0232593 A1    Sep. 13, 2012

Related U.S. Application Data

(60) Provisional application No. 61/450,188, filed on Mar. 8, 2011.

(51) Int. Cl.
*A61B 17/70* (2006.01)

(52) U.S. Cl.
CPC ......... *A61B 17/7049* (2013.01); *A61B 17/7052* (2013.01)

(58) Field of Classification Search
CPC ............. A61B 17/7049; A61B 17/705; A61B 17/7052
USPC .................................................. 606/250–253
See application file for complete search history.

(56) References Cited

U.S. PATENT DOCUMENTS

| | | | |
|---|---|---|---|
| 5,474,551 A * | 12/1995 | Finn et al. | 606/264 |
| 5,667,526 A | 9/1997 | Levin | |
| 5,702,393 A * | 12/1997 | Pfaifer | 606/328 |
| 5,727,899 A | 3/1998 | Dobrovolny | |
| 5,741,255 A * | 4/1998 | Krag et al. | 606/264 |
| 5,947,966 A | 9/1999 | Drewry et al. | |
| 6,017,306 A | 1/2000 | Bigliani et al. | |
| 6,096,039 A | 8/2000 | Stoltenberg et al. | |
| 6,110,173 A | 8/2000 | Thomas, Jr. | |
| 6,123,482 A | 9/2000 | Keller | |
| 6,132,430 A | 10/2000 | Wagner | |
| 6,171,311 B1 | 1/2001 | Richelsoph | |
| 6,238,396 B1 | 5/2001 | Lombardo | |
| 6,311,586 B1 | 11/2001 | Hirse | |
| 6,524,310 B1 | 2/2003 | Lombardo et al. | |
| 6,616,664 B2 | 9/2003 | Philips | |
| 6,736,775 B2 | 5/2004 | Phillips | |
| 6,866,664 B2 * | 3/2005 | Schar et al. | 606/252 |
| 7,314,331 B1 | 1/2008 | Koros et al. | |
| 7,553,279 B1 | 6/2009 | Phillips et al. | |
| 7,628,799 B2 * | 12/2009 | Richelsoph et al. | 606/250 |
| 7,666,210 B2 | 2/2010 | Franck et al. | |
| 7,744,632 B2 | 6/2010 | Usher | |
| 7,749,163 B2 | 7/2010 | Mulac et al. | |

(Continued)

*Primary Examiner* — Mary Hoffman
(74) *Attorney, Agent, or Firm* — Foley & Lardner LLP

(57) ABSTRACT

A spinal rod cross connector assembly for connection to adjacent spinal rods provides polyaxial positioning of polyaxial heads of the cross connector assembly relative to each spinal rod and which allows adjustment and fixation of the span of a cross connector or arm of the cross connector assembly between the two polyaxial heads through movement of the cross member relative to only one polyaxial head. Each polyaxial head has a clamp that provides attachment to the respective spinal rod and which allows the body of the polyaxial head to rotate relative thereto. Fixation of the orientation of a polyaxial head is achieved through placement and interaction of a set screw in the polyaxial head. The arm is preferably integral with and extends from a lateral side of one of the polyaxial heads. The second one of the polyaxial heads receives the arm and allows length adjustment relative thereto.

18 Claims, 3 Drawing Sheets

(56) References Cited

U.S. PATENT DOCUMENTS

| | | |
|---|---|---|
| 8,080,037 B2 | 12/2011 | Butler et al. |
| 8,241,334 B2 | 8/2012 | Butler et al. |
| 8,262,700 B2* | 9/2012 | Cho et al. ............... 606/250 |
| 2003/0114853 A1 | 6/2003 | Burgess et al. |
| 2005/0113831 A1 | 5/2005 | Franck et al. |
| 2005/0228377 A1 | 10/2005 | Chao et al. |
| 2006/0064093 A1 | 3/2006 | Thramann et al. |
| 2006/0206114 A1 | 9/2006 | Ensign et al. |
| 2007/0049932 A1 | 3/2007 | Richelsoph et al. |
| 2007/0083201 A1* | 4/2007 | Jones et al. ............... 606/61 |
| 2008/0086134 A1 | 4/2008 | Butler et al. |
| 2009/0204150 A1* | 8/2009 | Hochschuler et al. ........ 606/246 |
| 2011/0060367 A1* | 3/2011 | Stauber ............... 606/250 |
| 2011/0245872 A1* | 10/2011 | Nilsson ............... 606/250 |

\* cited by examiner

POSTERIOR CROSS CONNECTOR ASSEMBLY

RELATED APPLICATIONS

This patent application claims the benefit of and/or priority under 35 U.S.C. §119(e) to U.S. Provisional Patent Application Ser. No. 61/450,188 filed Mar. 8, 2011, entitled "Posterior Cross Connector Assembly" the entire contents of which is specifically incorporated herein by this reference.

BACKGROUND OF THE INVENTION

1. Field of the Invention

The present invention relates to relates to spinal fixation devices that are attached onto a patient's spine such as spinal rods and spinal rod screws (spinal rod assemblies) and, more particularly, to spinal cross connectors for attachment to adjacent spinal rods.

2. Background Information

There are many medical situations such as disease, injury, trauma or deformity, where it is necessary to align, hold, maintain and/or fix a desired relationship between adjacent vertebrae of the spine. In order to accomplish this goal, spinal surgeons utilize spine fixation devices that are attachable to the posterior of various adjacent vertebrae of the affected area of the spine. These spine fixation devices provide the desired relationship between adjacent vertebrae. Spine fixation devices typically include a spinal fixation element, such as a relatively rigid fixation rod (e.g. a spine or spinal rod) that is connected to adjacent vertebrae through attachment of the rod to anchor devices (e.g. bone screw/rod head assemblies) implanted into the vertebrae. As such, spine fixation devices may be termed spine fixation assemblies.

Typically, spine fixation rods are placed on opposite sides of the spinous process in a substantially parallel relationship. The spine fixation rods may have pre-determined contours according to properties of the target implantation site and/or with regard to a desired spatial, vertebral relationship. The bone screw/rod head assemblies are typically implanted into the pedicle or pedicle area of the vertebra. Once installed, the spine fixation assemblies hold the vertebrae in a secure spatial relationship.

It may also be necessary in some circumstances, however, such as in cervical spine fixation applications, to provide a cross connector at one or more points between the two spine fixation assemblies in order to provide additional stability to the structure. Particularly, adjacent spinal fixation rod assemblies can be made more robust by using a cross connector to bridge the pair of spinal rod assemblies.

While current spinal cross connectors are effective, problems exist such as in mounting and maintaining the cross connector in a desired position and orientation with respect to the spinal rods. Other problems also exist with current cross connectors such as height limitations, sizing, locking and ease of installation issues.

Accordingly, there presently exists a need for an improved spinal cross connector that can be easily installed, that securely attaches to and between installed spinal rods, and provides variation in positioning.

SUMMARY OF THE INVENTION

The present invention is a spinal rod cross connector assembly for connection to adjacent spinal rods of a spinal rod system. The spinal rod cross connector assembly provides independent polyaxial positioning and positional fixation of arbitrarily first and second polyaxial heads of the spinal rod cross connector assembly onto respective spinal rods. A cross connector of the spinal rod cross connector assembly is integral with and extends from the first polyaxial head and allows for adjustable connection to the second polyaxial head. This provides adjustment and fixation of the cross connector between the first and second polyaxial heads through translation of the cross member relative to the second polyaxial head. Each polyaxial head is configured to fixedly clamp onto the respective spinal rod while fixing the position (orientation) of the polyaxial head.

Each polyaxial head includes a preferably, but not necessarily, one-piece clamp which, through interacting geometry of the one-piece clamp with the interior configuration of the polyaxial head, provides fixation of the position and orientation of the polyaxial head on the spinal rod. Fixing the position and orientation of the second polyaxial head fixes both the position and orientation of the second polyaxial head on the spinal rod and fixes the translational position of the cross connector to the second polyaxial head.

Fixation of the polyaxial heads is achieved through receipt of a set screw or the like in the polyaxial head. The set screw interacts with the one-piece clamp of the polyaxial head which in turn interacts with the interior configuration of the polyaxial head to activate clamping. The cross connector preferably, but not necessarily, extends from a lateral side of the first polyaxial heads so as to be transverse with an implanted spinal rod. The second polyaxial head slidingly receives the cross connector and allows length adjustment relative thereto in order to hold the spinal rods in a fixed position relative to one another.

The first set screw of the first polyaxial head drives and fixes the first clamp onto the first spinal rod via interaction between the outside configuration of the clamp and the configuration of a lower interior portion of the first polyaxial head. The second set screw of the second polyaxial head contacts and drives the cross connector (which is received in the second polyaxial head) onto the second clamp which fixes the second clamp onto the second spinal rod. The second set screw thus fixes both the span between the first and second spinal rods (the length of the cross connector between the first and second polyaxial heads) and of the clamp onto the second spinal rod.

The cross member preferably, but not necessarily, has an upper flat that provides a contact surface for the second set screw, and a lower configured surface (e.g. a radial surface or a flat/planar surface) defining a contact surface for the clamp.

Preferably, but not necessarily, the clamps of the first and second polyaxial heads are each discrete components. The first clamp has a convex upper surface that interfaces with a concave lower surface of a respective set screw. The second clamp has a convex upper surface that interfaces with the configured (radial or planar) lower surface of the cross connector/arm. The relationship of the concave/radial/convex surfaces allows uniform force distribution during lockup at all angulation permutations.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

A description of the features, functions and/or configuration of the components depicted in the various figures will now be presented. It should be appreciated that not all of the features of the components of the figures are necessarily described. Some of these non-discussed features, if any, as well as discussed features are inherent from the figures. Other non discussed features may be inherent in component geometry and/or configuration.

DETAILED DESCRIPTION OF EMBODIMENTS OF THE INVENTION

Figure 1:
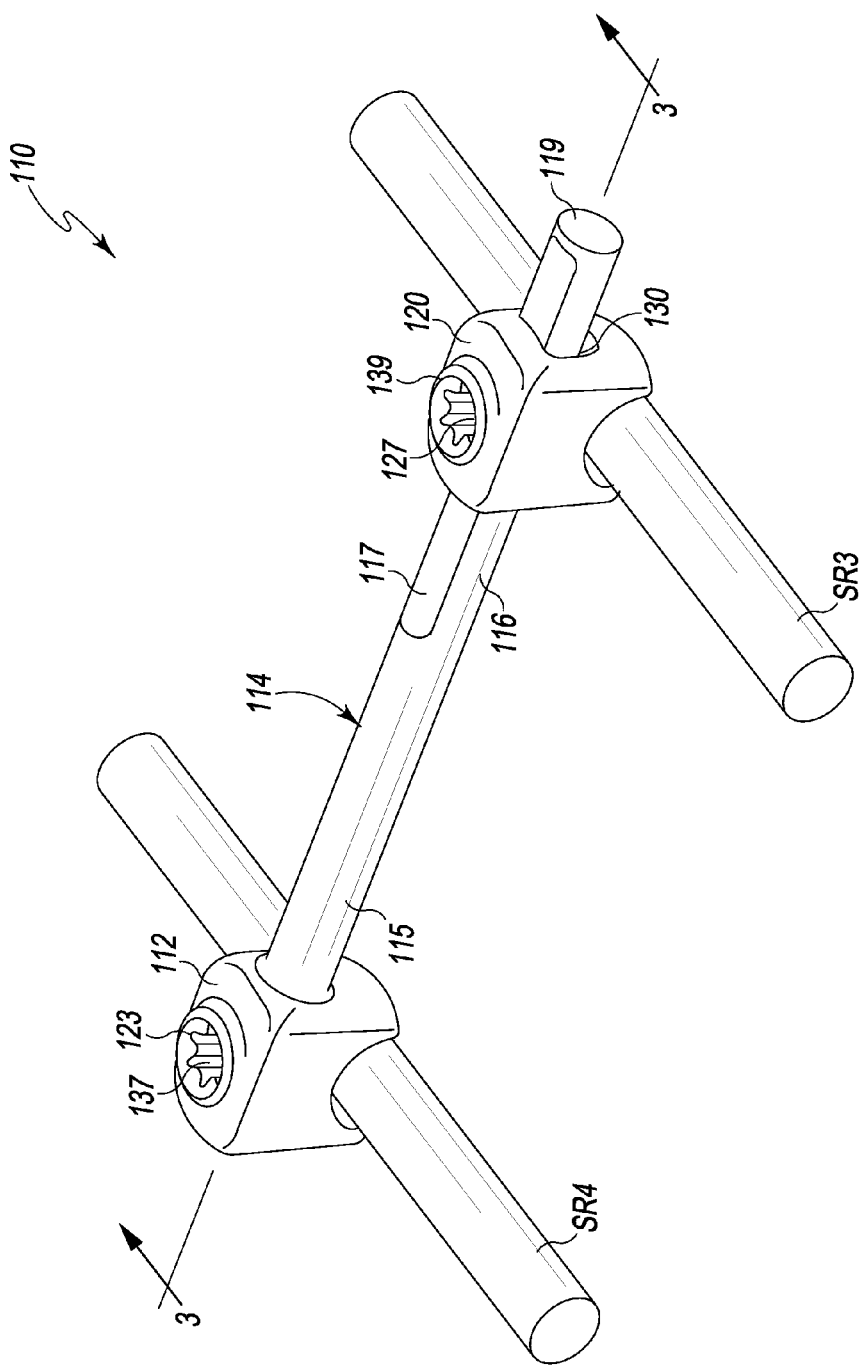
FIG. 1 is an isometric view of another embodiment of a cross connector assembly fashioned in accordance with the present principles shown mounted onto two spinal rods.
Figure 2:
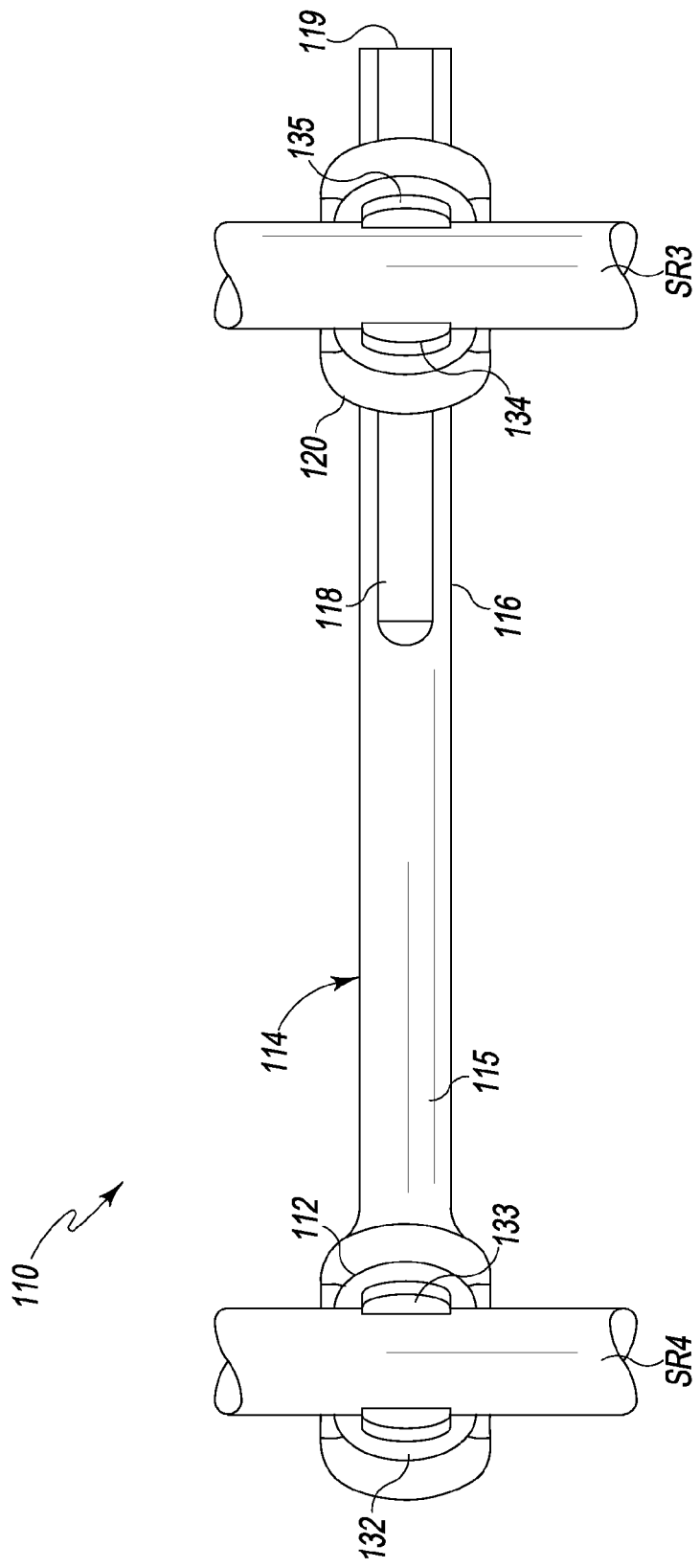
FIG. 2 is an enlarged bottom view of the cross connector assembly and spinal rods of FIG. 1.
Figure 3:
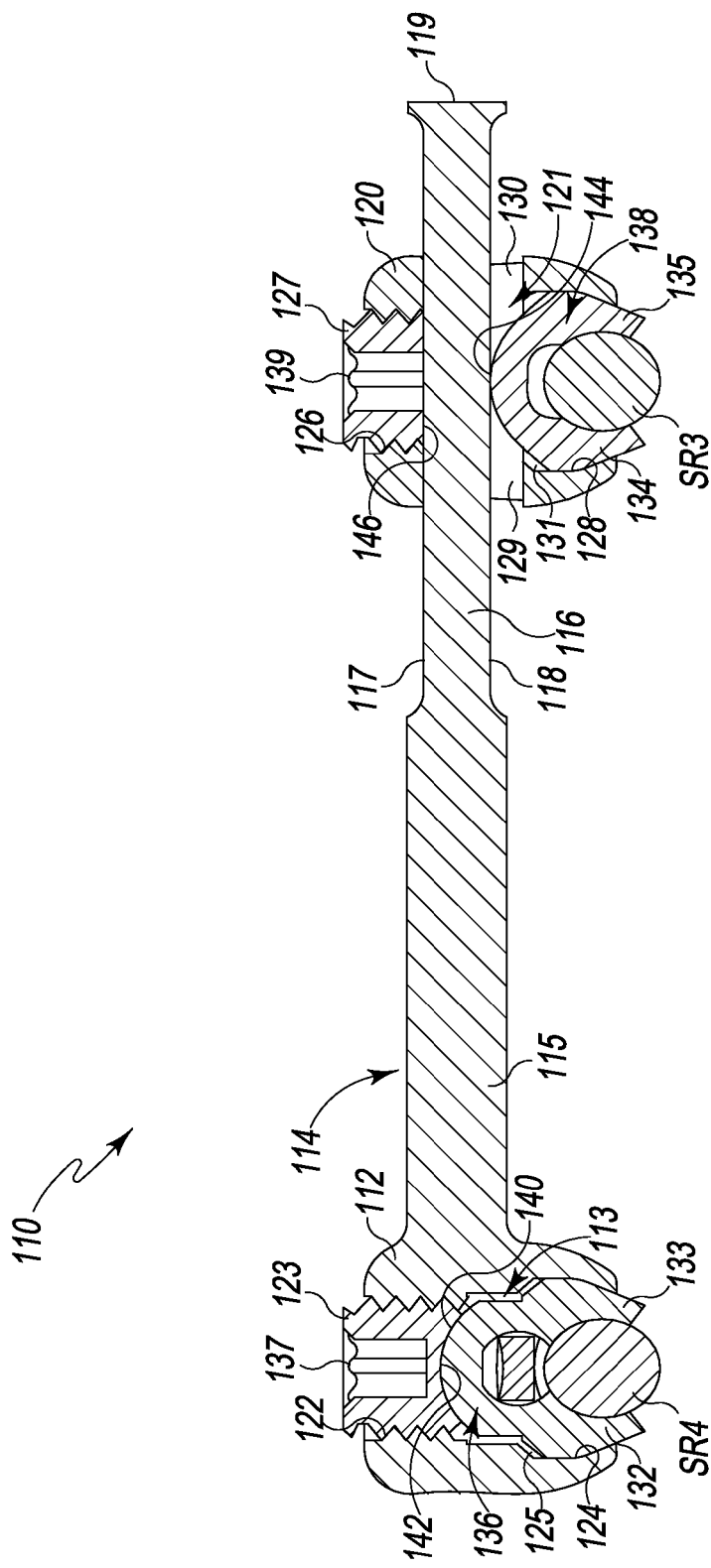
FIG. 3 is a sectional view of the cross connector assembly and spinal rods of FIG. 1 taken along line 3-3 of FIG. 1.

Referring to FIGS. 1-3, there is depicted an isometric view (FIG. 1) of an embodiment of a cross connector, cross connector assembly or cross connector construct (collectively, cross connector assembly), generally designated 110, a bottom view of the cross connector assembly 110 (FIG. 2), and a sectional view of the cross connector assembly 110 (FIG. 3) attached to two spine or spinal rods SR3 and SR4. The cross connector assembly 110 is used for various purposes in association with spinal rods such as to provide additional strength to a posterior construct for fixation of the spine that includes two laterally affixed spinal rods (e.g. SR3 and SR4). The cross connector assembly 110 is made from a biocompatible material such as titanium or stainless steel. However, other biocompatible material, materials or compounds may be used.

The cross connector assembly 110 has a first polyaxial head 112 that is adapted for connection to the spinal rod SR4. The first polyaxial head 112 has a bore 113 that extends from the top thereof to the bottom thereof. An upper portion 122 of the bore 113 is internally threaded while a lower portion 124 of the bore 113 is curved inwardly. The bore 113 also defines an interior 125 holding a clasp or clamp 136 having a generally horseshoe shape with an elongated top that defines an upper convex surface 140. The clasp 136 further defines first and second clasp or clamping portions 132, 133. The first and second clasp portions 132, 133 are each shaped on an inside surface thereof to grasp the spinal rod SR4 while an outside surface of the first and second clasp portions 132, 133 is shaped to interact with the lower portion 124—all in a clamshell or armature-like manner. Particularly, the outside surface of the first clasp portion 132 is curved in like manner to the curvature of the lower portion 124 while the outside surface of the second clasp portion 133 is likewise curved in like manner to the curvature of the lower portion 124. Each clasp portion 132, 133 is also thicker in a middle portion thereof in order for the clasp portions 132, 133 to clamp against and onto the spinal rod SR4 as the clasp portions 132, 133 interact with the lower portion 124 as described further below.

In order to have the clasp portions 132, 133 clamp or attach onto the spinal rod SR4 and thus hold the polyaxial head 112 onto the spinal rod SR4, a set screw 123 is provided. The set screw 123 includes external threads/threading that match the threading of the upper portion 122 of the bore 113. The set screw 123 also has a configured bore 137 that extends through the set screw 123. The configured bore 37 is shown as a hexagonal bore that receives a hexagonal driver (not shown). Other bore configurations, however, may be used. The set screw 123 has a concave lower surface 142 that interfaces with the convex upper surface 140 of the clasp 136 to provide a uniform force distribution during lockup of the clasp 136 (as described below) at all angulation permutations.

The set screw 123 is shown situated in the upper portion 122 of the polyaxial head 112 after it has been driven onto the clamp 136. As the set screw 123 is driven downwardly onto the clasp 136, the concave lower surface 142 of the set screw 123 contacts the convex upper surface 140 of the clasp 136. This causes the clasp portions 132, 133 to be driven downwardly into the curved lower portion 124 of the bore 113 forcing the clasp portions 132, 133 inwardly towards the spinal rod SR4 thereby clamping onto the spinal rod SR4. Additionally, the polyaxial head 112 is free to rotate relative to the clasp 136 while the set screw 123 has not been driven downwardly onto the clasp 136. This allows the polyaxial head 112 to rotate relative to the clasp 136/clasp portions 132, 133 and thus the spinal rod SR4 in order to change the orientation of the polyaxial head 112 relative to the spinal rod SR4. As the clasp portions 132, 133 are driven downwardly by the set screw 123 the clasp portions 132, 133 also lock the polyaxial head 112 from further rotation thus setting its rotational position relative to the spinal rod SR4.

As shown, an offset (e.g. a lateral offset) cross connector or arm 114 extends from a side of the first polyaxial head 112, preferably, but not necessarily, form a lateral side thereof. The arm 114 is also preferably, but not necessarily, integral with the first polyaxial head 112. The arm 114 is defined by a first portion 115 of a first diameter, and a second portion 116 of a second, smaller diameter. The second portion 116 includes a flat 117 on an upper surface thereof (i.e. upper flat 117) and a configured lower surface 118 thereof that is preferably a radial or concave surface (i.e. lower radial surface 118) or may be a flat (i.e. lower flat 118). The arm 114 has a length sufficient to extend to and across the spinal rod SR3 such that it is receivable in a second polyaxial head 120 (noting that the nomenclature first and second with respect to the polyaxial heads is arbitrary) that is adapted for connection to the spinal rod SR3. The arm 114 has a rounded end 119. Other configurations are contemplated.

The second polyaxial head 120 has a bore 121 that extends from the top thereof to the bottom thereof. An upper portion 126 of the bore 121 is internally threaded while a lower portion 128 of the bore 121 is curved inwardly. The bore 121 also defines an interior 131 holding a clasp or clamp 138 having a generally horseshoe shape that defines an upper convex surface 144. The clasp 138 further defines first and second clasp or clamping portions 134, 135. The first and second clasp portions 134, 135 are each shaped on an inside surface thereof to grasp the spinal rod SR3 while an outside surface of the first and second clasp portions 134, 135 is shaped to interact with the lower portion 128—all in a clamshell or armature-like manner. Particularly, the outside surface of the first clasp portion 134 is curved in like manner to the curvature of the lower portion 128 while the outside surface of the second clasp portion 135 is likewise curved in like manner to the curvature of the lower portion 128. Each clasp portion 134, 135 is also thicker in a middle portion thereof in order for the clasp portions 134, 135 to clamp against and onto the spinal rod SR3 as the clasp portions 134, 135 interact with the lower portion 128 as described further below.

The second polyaxial head 120 further includes a first lateral bore 129 and a second lateral bore 130 that receives and allows the arm 114 to extend therethrough. Particularly, the second portion 116 of the arm 114 extends through the first and second lateral bores 129, 130 and is allowed to laterally translate therein to provide lateral adjustability of the arm 114 relative to the second polyaxial head 120.

In order to have the clasp portions 134, 135 clamp onto the spinal rod SR3 and thus hold the second polyaxial head 120 onto the spinal rod SR3, a set screw 127 is provided. The set screw 127 includes external threads/threading that match the threading of the upper portion 126 of the bore 121. The set screw 127 also has a configured bore 139 that extends through the set screw 127. The configured bore 139 is shown as a hexagonal bore that receives a hexagonal driver (not shown). Other configurations, however, may be used. The set screw 127 further has a planar lower surface 146 that interfaces with the planar upper flat 117 of the second portion 116 of the arm 114 as the set screw 127 is driven onto the second portion 116 as described below.

The set screw 127 is shown situated in the upper portion 126 of the second polyaxial head 120 after it has been driven onto the upper flat 117 of the second portion 116 of the arm 114 while the lower surface 118 of the second portion 116 has been driven onto the upper convex surface 144 of the clamp 138. The downward force on the upper convex surface 144 causes the clasp portions 134, 135 to be driven downwardly into the curved lower portion 128 of the bore 121 forcing the clasp portions 134, 135 inwardly towards the spinal rod SR3 thereby clamping onto the spinal rod SR3. The curvature of the upper convex surface 144 provides a uniform force distribution during lockup of the clasp 138 at all angulation permutations. The lateral bores 129, 130 are sized to allow downward movement of the second portion 116 in order to have the second portion 116 contact and downwardly push the clamp 138 and thus the clamp portions 134, 135. Thus, as the set screw 127 is driven downwardly onto the upper flat 17, the lower surface 118 is driven downwardly onto the clasp portions 134, 135. In turn, the clasp portions 134, 135 are driven downwardly into the curved lower portion 128 of the bore 121 forcing the clasp portions 134, 135 inwardly towards the spinal rod SR3 thereby clamping onto the spinal rod SR3. Additionally, the second polyaxial head 120 is free to rotate relative to the clasp portions 134, 135 while the set screw 127 has not been driven downwardly. This allows the second polyaxial head 120 to rotate relative to the clasp 138 and the clasps 134, 135 and thus the spinal rod SR3 in order to change the orientation of the second polyaxial head 120 relative to the spinal rod SR3. As the clasp 138/clasp portions 134, 135 are driven downwardly by the set screw 127/second portion 116 the clasp portions 134, 135 also lock the second polyaxial head 120 from further rotation thus setting its rotational position relative to the spinal rod SR3.

The cross connector assembly 110 provides polyaxial positioning of both polyaxial heads 112, 120 relative to the respective spinal rods SR4, SR3 and adjustment and fixation of the span or length of the cross connector, member or arm 114 between the polyaxial heads 112, 120 through adjustment relative to only one polyaxial head rather than two polyaxial heads.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A spinal device for maintaining a spatial relationship between first and second spinal rods, the spinal device comprising:
    a first polyaxial clamp assembly configured for attachment to a first spinal rod, the first polyaxial clamp assembly having:
        a first housing with a first configured interior and a first bore extending from an upper surface of the first housing to a lower surface of the first housing and extending through the first configured interior, and
        a first clamp situated within the first configured interior and configured to clasp the first spinal rod when a first set screw is received in the first bore through the upper surface of the first housing and contacts the first clamp, and fix an orientation of the first housing relative to the first spinal rod, the first clamp comprising a one-piece clamp and has a convex upper surface that interfaces with a concave lower surface of the first set screw when the first set screw is received in the first bore of the first housing to provide clamping of the first clamp onto the first spinal rod;
    an arm extending from the first housing; and
    a second polyaxial clamp assembly configured for attachment to a second spinal rod, the second polyaxial clamp assembly having:
        a second housing with a second configured interior, a second bore extending from an upper surface of the second housing to a lower surface of the second housing and extending through the second configured interior, and a third bore extending from a first lateral side of the second housing to a second lateral side of the second housing, the arm adjustably received in the third bore, and
        a second clamp situated within the second configured interior and configured to clasp the second spinal rod when a second set screw is received in the second bore through the upper surface of the second housing, contacts the arm which then contacts the second clamp, to fix both the arm relative to the second housing and an orientation of the second housing relative to the second spinal rod, wherein the second clamp comprises a one-piece clamp and has a convex upper surface that interfaces with a configured lower surface of the arm which, via an upper surface of the arm, interfaces with a lower surface of the second set screw when the second set screw is received in the second bore of the second housing to provide clamping of the second clamp onto the second spinal rod.

2. The spinal device of claim 1, wherein the arm is integral with the first housing.

3. The spinal device of claim 2, wherein the arm extends from a lateral side of the first housing.

4. The spinal device of claim 2, wherein the arm extends laterally from the first housing.

5. The spinal device of claim 1, wherein the configured lower surface of the arm is configured as either or radial or planar.

6. A cross connector assembly for maintaining a spatial relationship between first and second spinal rods, the cross connector assembly comprising:
    a first polyaxial clamp assembly configured for fixed attachment to a first spinal rod and having:
        a first housing with a first configured interior and a first bore extending from an upper surface of the first housing to a lower surface of the first housing and extending through the first configured interior, and a first one-piece clamp situated within the first configured interior and configured to grasp the first spinal rod when a first set screw is received in the first bore through the upper surface of the first housing and applies pressure to the first one-piece clamp, and fix an orientation of the first housing relative to the first spinal rod, the first one-piece clamp comprising a convex upper surface that interfaces with a concave lower surface of the first set screw when the first set screw is received in the first bore of the first housing to provide clamping of the first clamp onto the first spinal rod;

an arm extending from a first lateral side of the first housing; and a second polyaxial clamp assembly configured for fixed attachment to a second spinal rod and having:

a second housing with a second configured interior, a second bore extending from an upper surface of the second housing to a lower surface of the second housing and extending through the second configured interior, and a third bore extending from a first lateral side of the second housing to a second lateral side of the second housing, the arm adjustably received in the third bore, and a second one-piece clamp situated within the second configured interior and configured to grasp the second spinal rod when a second set screw is received in the second bore through the upper surface of the second housing, applies pressure to the arm which then applies pressure the second one-piece clamp, to fix both the arm relative to the second housing and an orientation of the second housing relative to the second spinal rod, wherein the second one-piece clamp comprises a convex upper surface that interfaces with a configured lower surface of the arm which, via an upper surface of the arm, interfaces with a lower surface of the second set screw when the second set screw is received in the second bore of the second housing to provide clamping of the second clamp onto the second spinal rod.

7. The cross connector assembly of claim 6, wherein the arm is formed integral with the first housing.

8. The cross connector assembly of claim 7, wherein the arm extends perpendicular to the first lateral side of the first housing.

9. The cross connector assembly of claim 6, wherein:

the first one-piece clamp has first and second spinal rod clamping portions that are configured to contact the first spinal rod; and the second one-piece clamp has first and second spinal rod clamping portions that are configured to contact the second spinal rod.

10. The cross connector assembly of claim 9, wherein:

the first one-piece clamp has a convex upper surface that interfaces with a concave lower surface of the first set screw when the first set screw is received in the first bore of the first housing; and the second one-piece clamp has a convex upper surface that interfaces with a configured lower surface of the arm which, via an upper surface of the arm, interfaces with a lower surface of the second set screw when the second set screw is received in the second bore of the second housing.

11. The cross connector assembly of claim 10, wherein the configured lower surface of the arm is configured as either or radial or planar.

12. The cross connector assembly of claim 10, wherein the configured lower surface of the arm is planar, and the upper surface of the arm is planar.

13. The cross connector assembly of claim 10, wherein:

the first one-piece clamp is rotationally retained in the first interior of the first housing; and the second one-piece clamp is rotationally retained in the second interior of the second housing.

14. The cross connector assembly of claim 10, wherein:

the first bore of the first housing is threaded from the upper surface of the first housing to the first interior of the first housing for reception of the first set screw; and the second bore of the second housing is threaded from the upper surface of the second housing to the second interior of the second housing for reception of the second set screw.

15. A cross connector assembly for connection between first and second spinal rods, the cross connector assembly comprising:

a first polyaxial head configured for fixed attachment to a first implanted spinal rod and having a first configured interior, and a first bore extending from an upper surface of the first polyaxial head to a lower surface of the first polyaxial head and in communication with the first configured interior;

a first one-piece clamp situated within the first configured interior and configured to grasp the first spinal rod when a first set screw is received in the first bore through the upper surface of the first polyaxial head and applies pressure to the first one-piece clamp, and fix an orientation of the first polyaxial head relative to the first spinal rod, the first one-piece clamp comprising a convex upper surface that interfaces with a concave lower surface of the first set screw when the first set screw is received in the first bore of the first housing to provide clamping of the first clamp onto the first spinal rod;

an arm extending from and integral with a first lateral side of the first polyaxial head;

a second polyaxial head configured for fixed attachment to a second implanted spinal rod and having a second configured interior, a second bore extending from an upper surface of the second polyaxial head to a lower surface of the second polyaxial head and extending through the second configured interior, and a third bore extending from a first lateral side of the second polyaxial head to a second lateral side of the second polyaxial head, the arm adjustably received in the third bore; and a second one-piece clamp situated within the second configured interior and configured to grasp the second spinal rod when a second set screw is received in the second bore through the upper surface of the second polyaxial head, applies pressure to the arm which then applies pressure the second one-piece clamp, to fix both the arm relative to the second polyaxial head and an orientation of the second polyaxial head relative to the second spinal rod, wherein the second one-piece clamp comprises a convex upper surface that interfaces with a configured lower surface of the arm which, via an upper surface of the arm, interfaces with a lower surface of the second set screw when the second set screw is received in the second bore of the second housing to provide clamping of the second clamp onto the second spinal rod.

16. The cross connector assembly of claim 15, wherein the arm extends perpendicular from the first lateral side of the first polyaxial head.

17. The cross connector assembly of claim 15, wherein:
the first one-piece clamp has first and second spinal rod clamping portions that are configured to contact the first spinal rod; and
the second one-piece clamp has first and second spinal rod clamping portions that are configured to contact the second spinal rod.

18. The cross connector assembly of claim 17, wherein:
the first one-piece clamp has a convex upper surface that interfaces with a concave lower surface of the first set screw when the first set screw is received in the first bore of the first polyaxial head; and
the second one-piece clamp has a convex upper surface that interfaces with a configured lower surface of the arm which, via an upper surface of the arm, interfaces with a lower surface of the second set screw when the second set screw is received in the second bore of the second polyaxial head.

* * * * *